United States Patent
Silfversparre et al.

(10) Patent No.: US 7,198,936 B2
(45) Date of Patent: Apr. 3, 2007

(54) METHOD FOR GROWTH OF BACTERIA, MINIMISING THE RELEASE OF ENDOTOXINS FROM THE BACTERIA INTO THE SURROUNDING MEDIUM

(75) Inventors: Gustav Silfversparre, Trelleborg (SE); Sven-Olof Enfors, Sollentuna (SE); Ling Han, Stockholm (SE); Lena Häggström, Sollentuna (SE); Harald Skogman, Falsterbo (SE)

(73) Assignee: Novozymes Biopharma AB, Lund (SE)

( * ) Notice: Subject to any disclaimer, the term of this patent is extended or adjusted under 35 U.S.C. 154(b) by 44 days.

(21) Appl. No.: 10/415,332

(22) PCT Filed: Oct. 30, 2001

(86) PCT No.: PCT/SE01/02370

§ 371 (c)(1),
(2), (4) Date: Aug. 13, 2003

(87) PCT Pub. No.: WO02/36746

PCT Pub. Date: May 10, 2002

(65) Prior Publication Data

US 2004/0029253 A1    Feb. 12, 2004

(30) Foreign Application Priority Data

Oct. 31, 2000    (SE) ................. 0003958-6

(51) Int. Cl.
*C12N 1/12*    (2006.01)
*C12N 1/20*    (2006.01)
(52) U.S. Cl. .............. 435/252.1; 435/252.33; 435/243
(58) Field of Classification Search ........ 435/243, 435/252.1, 252.33
See application file for complete search history.

(56) References Cited

U.S. PATENT DOCUMENTS

| | | | |
|---|---|---|---|
| 4,885,168 A | 12/1989 | Hashimoto et al. | |
| 5,487,980 A | 1/1996 | Swartz | |
| 2003/0108997 A1* | 6/2003 | Mahr et al. | 435/69.1 |

FOREIGN PATENT DOCUMENTS

| | | |
|---|---|---|
| EP | 0 289 129 A2 | 11/1988 |
| EP | 0 291 968 B1 | 11/1988 |
| EP | 0 333 474 A2 | 9/1989 |
| EP | 0 337 243 A1 | 10/1989 |
| EP | 0 407 037 B1 | 1/1991 |
| EP | 0 528 635 B1 | 2/1993 |
| EP | 0 775 150 B1 | 5/1997 |
| EP | 0 867 453 A2 | 9/1998 |
| WO | WO89/03885 | 5/1989 |

OTHER PUBLICATIONS

Weber-Frick et al. (Zenralbi Bakteriol Mikrobiol Hyg, 1988 vol. 187 No. 1, pp. 56-69).*
D. Riesenberg et al., "High-Cell-Density Cultivation of Microorganisms", Appl. Microbiol Biotechnol, vol. 51, pp. 422-430, (1999).
G. Walsh et al., "Protein Biotechnology", Therapeutic Proteins: Special Aspects, John Wiley & Sons, New York, pp. 18 and 148-153.
P.A. Mackowiak, "Relationship Between Growth Temperature and Shedding of Lipopolysaccharides by Gram-Negative Bacilli", Eur. J. Clin. Microbiol., vol. 3, No. 5, pp. 406-410, Oct. 1984.
S. Bauer et al., "Pilot Scale Exponential Growth of *Escherichia coli* W to High Cell Concentration With Temperature Variation", Biotechnology and Bioengineering, vol. XVIII, pp. 839-846, (1976).
D. Petsch et al., "Endotoxin Remopval From Protein Solutions", Abstract of Journal of Biotechnology, vol. 76, p. 76, (Jan. 21, 2000), abstract only.
N.V. Stukalova et al., "Influence of the Conditions of the Controlled Cultivation of *Neisseria meningitidis* on the Yield of Lipopolysaccharide", I.I. Abstract of Zhumal Mikrobiologii Epidemiologii Immunobiologii, 5, (1995), Abstract only.

* cited by examiner

*Primary Examiner*—Robert A. Zeman
(74) *Attorney, Agent, or Firm*—Finnegan, Henderson, Farabow, Garrett & Dunner, L.L.P.

(57) ABSTRACT

The invention relates to a method for growth of bacteria, such as Gram negative bacteria and its corresponding supernatant. The bacteria are cultivated without substantial release of endotoxins from the bacteria into the surrounding medium. Thereby the need of purification steps necessary to remove endotoxins are reduced or eliminated such as when the bacteria are producing a product which later on should be administered to a mammal, such as a human. The bacteria are also cultivated without substantial formation of acetic acid. The level of the carbon/energy source is controled during the cultivation and oxygen limitation is avoided through regulation of the temperature. The method may be used for cultivation of bacterial in fermenters.

11 Claims, No Drawings

METHOD FOR GROWTH OF BACTERIA, MINIMISING THE RELEASE OF ENDOTOXINS FROM THE BACTERIA INTO THE SURROUNDING MEDIUM

FIELD OF INVENTION

The invention relates to a method for growth of bacteria, such as Gram negative bacteria and its corresponding supernatant. The bacteria are cultivated without substantial release of endotoxins from the bacteria into the surrounding medium and without substantial formation of acetic acid.

BACKGROUND OF INVENTION

Bacterial endotoxins are potent pyrogens that often produces fever reactions when administered to patients. The endotoxin is an integral component of the outer cell membrane of Gram negative bacteria. It exists in its natural stage as a complex of lipid, carbohydrate and protein.

The outer membrane of Gram negative bacteria serves as an outer barrier through which materials must penetrate, if they are to reach the cell. It is selectively permeable. Grown in vitro Gram negative bacteria often release large amounts of endotoxins, up to approximately 1000 mg/ml.

Fermentation has long been a key technology for mass production of products in Gram negative bacteria. An economic fermentation process usually has to demonstrate an optimal cell production, maximum accumulation of the desired product and minimum consumption of nutrients. In most industrial applications, fed-batch cultures have been found preferable over batch cultures due to that the fed-batch technique provides means to obtain higher productivity and higher product concentration compared to batch cultures. This is achieved by controlling the nutrient feeding to regulate the biological reaction rates like e.g. those of energy metabolism (respiration) and growth in a desired range. It is necessary to control the energy metabolism to avoid oxygen limitation in the culture. Controlled feeding of the energy/carbon source is also an effective method to avoid acetic acid accumulation due to overflow metabolism. Production of acetic acid reduces the yield of biomass and the desired product or products.

However, regulation performed solely by the nutrient feeding, usually by a carbon/energy source such as glucose, results in an excessive release of endotoxins into the medium in which the Gram negative bacteria is cultivated. The release of endotoxins results in the need of several purification steps to eliminate the undesired endotoxins from the product prior to use, when the product is to be administered to mammals (e.g. humans).

Endotoxins in large quantities can cause shock, severe diarrhea, fever and leuopenia followed by leukocytosis, elicit the Schwartzman and Sanarelli-Schwartzman phenomena and in severe cases, death of recipient patients. Therefor it is highly important to eliminate the endotoxins prior to use.

A number of methods for removal of endotoxins are known in the art, such as rinsing with nonpyrogenic solution (Feldstine et al., 1979, J. Peranter. Drug. Assoc., 33:12), distillation, ultrafiltration using membranes rated by molecular weight exclusion (Sweadner et al., 1977, Appl. Environ. Microbiol., 34:382, reverse osmosis using thin cellulose acetate or polyamide materials (Neslon, 1978, Pharm. Technol., 2:46), electrostatic attraction (Gerba et al., 1980, Pharm Technom., 4:83), hydrophobic attraction using aliphatic polymers (Robinson et al., 1985; Parental Drug Association, 54–69), adsorption using activated carbon (Berger et al., 1956, dv. Chem. Ser., 16:169) and affinity chromatography (Soter, 1984, Bio/Technol, 12:1035) among others.

The purification steps presently available for the removal of endotoxins are expensive and several steps are necessary for the satisfactory removal of the endotoxins. During the removal of the endotoxins, all the purification steps results in a reduced amount of the biological product of interest as well as the endotoxins.

The invention provides an improved method to be used for the cultivation of bacteria such as Gram negative bacteria without substantial release of endotoxins and without substantial formation of acetic acid. Thereby the need of purification steps for removal of the endotoxins is reduced or eliminated and still the biomass yield is high as well as the accumulation of the desired produced product.

SUMMARY OF THE INVENTION

This application discloses improved methods for the growth of bacteria, in particular Gram negative bacteria such as *E. coli*, without substantial release of endotoxins from the bacteria into the surrounding medium and without substrate limitation, such as the carbon/energy source, of the biological reaction rates like e.g. those of energy metabolism (respiration) and the growth rate. Thereby the need of purification steps is reduced or eliminated for the removal of the toxic endotoxins.

Furthermore the invention provides a method which prevents accumulation of acetic acid to a level, which normally results in a reduced amount of biomass and desired product yields of the bacteria.

Accordingly, in a first aspect the invention relates to a method for growth of bacteria for the production of a product, with a minimal amount of endotoxins released, comprising following steps; preparing a culture of bacteria and a growth medium including a carbon/energy source; cultivating the culture at a suitable initial temperature; maintaining the carbon/energy source at a level minimising the endotoxin release and acetic acid formation and monitoring the oxygen limitation status of the culture of the bacteria; reducing the initial temperature without limiting the carbon/energy source; maintaining conditions where oxygen limitation is avoided by increasing and/or reducing the temperature during cultivation and harvesting the product from the culture having a minimal amount of endotoxins.

In another aspect the invention relates to a method for growth of bacteria for the production of a product, with a minimal amount of endotoxins released, comprising following steps; preparing a first culture of bacteria and growth medium comprising a limiting carbon/energy source arranged as a chemostat, and a second continuous culture of bacteria and growth medium; feeding the second culture with the outlet culture from the chemostat; cultivating of the second culture continuously fed with the limiting carbon/energy source of the chemostat so that substrate limitation is avoided; cultivating at a defined temperature to avoid oxygen limitation in the second culture; harvesting the product from the outlet culture of the second culture having a minimal amount of endotoxins.

In another aspect the invention relates to a supernatant from a bacterial culture having an amount of the endotoxins of <100 mg/l.

The disclosed improved method for the growth of bacteria without substantial release of endotoxins and acetic acid formation from the bacteria into the medium, provides a method which reduce or eliminates the numbers of purification steps necessary to remove the endotoxins after growth of the bacteria and maintaining the biomass and desired product yields of the bacterial strain.

Hereby, a successful bacterial cultivation process, to produce high-quality biological products in an improved Good Manufacture Practice (GMP) culturing process is obtained. Furthermore, the process is less expensive as compared to the methods available today for the production of a product within bacteria, which release endotoxins.

DETAILED DESCRIPTION OF THE INVENTION

In the context of the present invention the following definitions apply:

The term "growth medium" is intended to mean a medium used for the growth of bacteria in a culture comprising components necessary for growth of the bacteria, such as a carbon/energy source.

The term "component" is intended to mean a component used in a conventional growth medium for growth of bacteria. Examples of components for growth of bacteria are found in table 1. Other components are ions like phosphate and magnesium ions and a carbon/energy source. Examples of carbon/energy sources are found in Table 1.

The term "substrate limitation" is intended to mean conditions under which the concentration of one or more medium components (i.e. a substrate) is so low that its concentration limits the growth rate.

The term "fermentation" is intended to mean production of products produced by bacteria, such as Gram negative bacteria. The fermentation is performed in fermenters, such as in batch-, fed-batch-, or continuous cultures.

The term "overflow metabolism" is intended to mean the excretion of the partially oxidized acetic acid that occurs when the glucose concentration exceeds a critical value, specific for each organism (Xu et al, 1999, Appl. Microbiol. Biotechnol. 51(5): 564–71). Production of acetic acid reduces the yield of biomass and the desired product(s) and high concentrations, mostly >10 g/l of acetic acid are toxic to the organism. Overflow metabolism is normally avoided by keeping the carbon/energy source concentration low as it is done in fed batch cultures by controlling the nutrient feeding.

The term "dissolved oxygen tension" (DOT) is intended to mean the partial pressure of oxygen in equilibrium with the culture that is measured e.g. with an oxygen electrode immersed in the medium. DOT is an indirect measure of the dissolved oxygen concentration.

The term "oxygen limitation" is intended to mean conditions under which the concentration of dissolved oxygen is so low that other electron acceptors than oxygen must be used by the microorganisms when re-generating the cofactors NAD+ and FAD. Under these conditions anaerobic respiration is used for the energy generation. For $E.\ coli$ this results in excretion of the mixed acid fermentation products; succinate, lactate, ethanol, acetate and formate. Conditions when oxygen limitation occurs, can be monitored by direct measurement of the dissolved oxygen tension (DOT) or indirectly by on-line calculation of the oxygen consumption rate (OCR) e.g. based on on-line monitoring of the concentration of oxygen in the outlet air flow (S. O. Enfors, 1994, Bioprocess Technology Fundamentals and Applications). Alternatively oxygen limitation can be avoided by control of the temperature at set point value or a pre set temperature profile. In these cases the set point value and the temperature profile has to be determined from experiments The term "set point" is intended to mean the critical value of the measured parameters used to assess that the culture is not oxygen limited, e.g. the: DOT or the oxygen concentration in the outlet air.

The term "chemostat" is intended to mean a continuous culture with a fixed flow rate and with substrate limitation that is achieved by means of the concentration of substrate in the supplied stream of medium.

TABLE 1

Examples of medium components

| Carbon/energy source | N sources | Vitamin sources |
|---|---|---|
| Sucrose | Ammonia | Yeast extract |
| Glucose | Ammonium sulphate | Distillers soluble |
| Lactose | Ammonium nitrate | Whey |
| Starch syrup | Corn steep liquor (CSL) | |
| Starch (corn-, potato-) | Soy meal | |
| Malt extract | Fish meal | |
| Grains | Peanut meal | |
| Molasses (cane-, beet-) | Distillers soluble | |
| Whey | Peptones of casein, soy, fish, meat. | |
| Alcohols (methanol, ethanol) | | |
| Glycerol | | |
| Lignocellulose | | |

Description of the Culturing Process for Growth of Bacteria

The invention relates to methods to be used for growth of bacteria for the production of one or more products with a minimal amount of endotoxins released from the bacteria, preferably production by fermentation.

Additionally, the methods according to the invention reduces overflow metabolism (as defined above). Thereby accumulation of acetic acid to high concentrations (concentration >10 g/l), is prevented.

The methods may be used alone or in combination with other methods for growth of bacteria, such as batch culturing without any carbon/energy source limitation, carbon/energy source limited fed-batch culturing and continuous culturing in which the carbon/energy source concentration is maintained at a level minimising the endotoxin release. For example $Escherichia\ coli$ may be cultivated using $\geq 25$ mg/l of glucose as the carbon/energy source and a specific growth rate of $\geq 0.05\ h^{-1}$.

In one embodiment of the invention the bacteria are endotoxin producing bacteria, which release the endotokins into the growth medium during substrate (a component of the growth medium such as the carbon/energy source) limited cultivation. Preferably the bacteria are Gram negative bacteria, such as $Enterobacteriaceae$. Preferably the bacteria is $Escherichia\ coli$ ($E.\ coli$), such as $E.\ coli$ K12 or the $E.\ coli$ K12 derivative W3110.

Furthermore, the bacteria used according to the invention produces a product or products, such as one or more recombinant DNA product(s). Preferably the bacteria produces one or more protein(s) or one or more polypeptide(s) or mixtures thereof. Most preferably the product(s) is/are produced by the $E.\ coli$ strain W3110 and the preferred production method is fermentation. Mutant cells from the above-mentioned bacteria may also be employed. The product(s) of interest is/are preferably recovered from the culture medium as a secreted product(s), although it may also be recovered from the cell lysate after disintegration of the cells.

The bacteria are grown under controlled conditions, such as a defined control of pH, aeration, agitation, DOT-value, temperature, time conditions and growth medium. Control of the growth medium may be nutrient type and the concentrations of the components, such as the carbon/energy source in the growth medium. Furthermore, the culturing process may be performed by fermentation, using conventional fermenters. Fermentation processes are known for those skilled in the art.

The cultivation conditions may be divided into two steps which may be organised either as two time-separated steps in a fed-batch culturing process or as two different cultivation steps, e.g. in two serially connected fermenters in a continuous culturing process.

In one embodiment of the invention a fed-batch configuration may be used. According to that embodiment, the above mentioned bacteria may be added to the growth medium to an initial concentration within the range of approximately 0.01–5 g/l (0.1–10% of the final dry weight), at a suitable initial temperature, preferably within the range of 20–40° C., more preferably at 30–37° C., such as at 35° C., defined pH control, addition of oxygen and under agitation. The growth is performed under aseptic conditions. During the first cultivation phase (step 1) in the fed-batch culturing process there is an approximately constant high specific growth rate and hence a relatively high carbon/energy source concentration minimising the endotoxin release. For example, the bacterial strain *Escherichia coli* may be cultivated using $\geq 25$ mg/l glucose as the carbon/energy source at a specific growth rate of $\geq 0.05$ $h^{-1}$. During the first cultivation phase the oxygen consumption rate of the culture increases exponentially. As a consequence of this the DOT value will decrease. At a cell density of approximately 10 g/l (the value depends on the growth rate and the oxygen transfer capacity in the fermenter) it becomes necessary to control the oxygen consumption rate (OCR) to avoid oxygen limitation. When using DOT measurements to monitor the oxygen limitation this point correlates to that the set point DOT value is reached. Said set point DOT value is a set point DOT value of $\leq 90\%$, preferably $\leq 50\%$, more preferably $\leq 30\%$ and most preferably 10–30%. Alternatively the DOT value may be regulated at a set point by increasing the aeration and/or stirrer speed until maximum values for aeration and stirrer speed are reached. When using OCR calculations to monitor oxygen limitation, a set point value of the oxygen concentration in the outlet air is used. The set point then depends on the oxygen transfer capacity of the fermenter and on the air flow rate and it has to be established based on previous experiments where the correlation between DOT and the oxygen concentration in the outlet air has been determined for the process conditions used.

The cultivation then enters the next cultivation phase (step 2) of the cultivation process, where the biological reaction rates like e.g. those of energy metabolism (respiration) and growth are controlled by the cultivation temperature in contrast to the standard fed-batch cultivations where these parameters are controlled by the nutrient feeding (normally the carbon/energy source). The cultivation temperature of the bacteria is then controlled by monitoring either the DOT or the oxygen concentration in the outlet air, such that if oxygen limitation according to the criteria described above is observed by either DOT or outlet oxygen concentration measurements, the temperature is decreased from the initial temperature. The temperature may be decreased by one or more degrees up to a maximum of around 25° C. decrease until no oxygen limitation occurs according to above described criteria. The decrease of the temperature, which is necessary to obtain the expected result according to the invention, is dependent on the bacterial strain among other things and may vary within the range of 1° C. up to 25° C. If the DOT or outlet oxygen concentration value is above the setpoint value, the temperature is increased, within the above mentioned intervals until the set point value is reached again. Alternatively manual temperature control or a temperature profile based on empirical data known not to give oxygen limitation can be applied to avoid oxygen limitation.

Addition of the carbon/energy source (see table 1) during step 2 prevents substrate limitation and thereby minimises the release of endotoxins from the bacteria. However, the controlled addition of the carbon/energy source also prevents the formation of acetic acid caused by the overflow metabolism. Thereby the growth of the bacteria and product formation is maintained. Preferably the acetic acid formation is reduced to <10 g/l. The carbon/energy source is added to the bacterial culture to a final concentration within the range of from about 0.025 to about 5 g/l, (0.025–3 g/l), such as 0.025–2 g/l, (0.025–1 g/l) or 0.025–0.5 (0.025–0.25 g/l). The carbon/energy source may be sugar, such as glucose or any other suitable sugar or mixtures thereof. The carbon/energy source may be obtained from any suitable source such as, corn, sugar beets, lignocellulose and sugar cane (see e.g. table 1.).

The growth of the bacteria mostly continues for 20–40 hours, until a cell concentration, normally within the range of 20–50 g/l and the product(s) is/are then harvested.

In another embodiment a continuous configuration culturing process may be used to realise the invention. According to that embodiment, two fermenters are connected in a sequence so that the outlet medium of the first fermenter comprising the first culture of bacteria and growth medium enters the second fermenter comprising the second culture of bacteria and growth medium. The first fermenter is operated as a conventional substrate limited chemostat. A component of the medium such as a carbon/energy source, including glucose or another medium component, may be used for substrate limitation in the chemostat. The carbon/energy source concentration is controlled by selection of a suitable dilution rate to provide a concentration high enough to prevent excessive release of endotoxin. For example, *Escherichia coli* may be cultivated using be $\geq 25$ mg/l glucose as the carbon/energy source and a specific growth rate of $\geq 0.05$ $h^{-1}$ in the first fermenter. The outlet medium from the first fermenter is continuously fed into the second fermenter. Addition of the carbon/energy source limiting in the first fermenter is made to the second fermenter to permit an increased cell concentration and avoid substrate limitation. The carbon/energy source is added to the bacterial culture to a final concentration from about 0.025 to about 5 g/l, (0.025–3 g/l), such as 0.025–2 g/l, (0.025–1 g/l) or 0.025–0.5 (0.025–0.25 g/l). Thereby the release of endotoxins and the formation of acetic acid are substantially reduced. To prevent oxygen limitation in the second fermenter the temperature can be regulated based on measurement of DOT or the oxygen concentration in the outlet air as described above. Alternatively a fixed temperature is applied, chosen from empirical data so that oxygen limitation is avoided. The outlet medium from the second fermenter containing the product with a minimal amount of endotoxins is then harvested.

Additionally the harvested bacterial culture contains a biomass of $\geq 15$ g/l, preferably $\geq 20$ g/l, more preferably $\geq 25$ g/l, most preferably $\geq 30$ g/l.

Another embodiment of the present invention relates to a supernatant obtained from a culture of bacteria cultivated according to the above mentioned methods for cultivation. The supernatant may have an amount of endotoxins which is ≦100 mg/l (≦75 mg/l), such as ≦50 mg/l (≦25 mg/l) or ≦15 mg/l, ≦10 mg/l or ≦2 mg/l.

According to a further embodiment of the invention the bacteria are used for mass production of products produced by the bacteria such as native or recombinant proteins or peptides, for example enzymes, hormones or artificial antibodies, vectors for gene therapy, antibiotics, insecticides, nucleotides, vaccines, vitamins and other industrial products or raw materials or mixtures thereof. The products may be naturally produced by a wild type bacteria or produced by a bacteria after modification, such as by recombinant techniques or any other suitable technique.

The cultivation equipment including necessary control means to realise this invention can be purchased from manufacturers of standard fermenters, for instance from Belach Bioteknik AB, Stockholm, Sweden.

The invention provides an improved method for growth of bacteria, such as in a fermenter in which the endotoxin production by the bacteria is substantially reduced. Thereby purification steps for the removal of the toxic endotoxins is reduced such as in the case when the produced product is to be used for a mammal.

Additionally the formation of acetic acid during the growth of the bacteria is substantially reduced by the use of controlled addition of the carbon/energy source and thereby biomass yield and the product production is maintained without influences from acetic acid formation.

The Control Strategy for the Fed-batch Configuration

The specific culturing process may be arranged as follows: The value of the controlled variable, DOT or oxygen concentration in the outlet air, is controlled by a conventional temperature mean regulator such that the input value from DOT or the oxygen concentration in the outlet air can control the temperature regulator and thereby the temperature through a standard control software (Åström and Hägglund., 1995, PID Controllers: Theory, Design and Tuning, second edition. Instrument Society of America, Research Triangle Park, N.C.). The equipment including necessary temperature regulator and set point value means can be purchased from manufactures of standard fermenters, for instance Belach Bioteknik AB, Stockholm, Sweden. The design and tuning of such a temperature regulator are known for those skilled in the art.

The temperature regulator is designed such that if the measured value is below the set-point value, the temperature is decreased and if the measured value exceeds the set point value, the temperature is increased.

The above control strategy, makes it possible to obtain a high cell density of a culture without limiting the biological reaction rates, like e.g. those of energy metabolism (respiration) and growth by means of the inflow rate of any medium component (e.g. table 1) in step 2 of the fed-batch culturing process. At the same time the endotoxins released from the bacteria is kept to a minimum, such as ≦100 mg/l, (≦75 mg/l), ≦50 mg/l, ≦25 mg/l, ≦15 mg/l, ≦10 mg/l or ≦2 mg/l. By the above strategy the consumption of oxygen is maintained more or less constant and the specific growth rate is decreased while the cell concentration is increased without any substrate limitation.

EXAMPLE 1

Control Fermentation with *E. coli* W3110

Bacterial Strain; The *E. coli* K12 strain W3110 [F⁻, IN(rrnD-rrnE)], (Genetic Stock Center, Yale University, New Haven, Conn.).

Media; Mineral salt medium with following composition 2.0 g/l $Na_2SO_4$, 2 g/l $(NH_4)_2SO_4$, 1.5 g/l $NH_4Cl$, 3 g/l $Na_2HPO_4 \times 2H_2O$, 7 g/l $KH_2PO_4$, 1 g/l $(NH_4)_2$—H-citrate and 0.1 g/l thiamin. The medium also contained 2 ml/l of 1M $MgSO_4$ and 2 ml/l of trace components (Xu B., at al., Modelling of overflow metabolism in batch and fed-batch cultures of *Escherichia coli.*, Biotechnol. Progress 15, 81–90, 1999).

The initial glucose concentration was 2.5 g/l. The pH was set to 6.8 prior to sterilisation by the addition of NaOH and adjusted prior to fermentation by the addition of ammonia (25%). An inoculum culture of 500 ml was run in shake flasks until the cell dry weight was about 0.3 g/l. The feed solution for the fed-batch cultivation included two times of the above mentioned salt concentrations and glucose at a concentration of 500 g/l. The *E. coli* strain W3110 was cultivated in an 8 liter standard laboratory fermenter obtained from Belach Bioteknik AB, Stockholm. The liquid volume at the beginning of the fed-batch culturing process was 4.5 l, and the culturing process was controlled as follows. When the initial glucose was consumed after about 4 hours, feeding was started at a rate of 10 ml/h and the glucose feed rate was increased exponentially to permit exponential growth at about $\mu=0.3/h$ without formation of acetic acid. The temperature was 35° C. throughout the culturing process. The aeration rate was 1 VVM (volume of air per volume of medium per minute) and the stirrer speed was 600 rpm.

When the DOT value reached about 50% the feed rate was kept constant until the end of the culturing process, which also resulted in approximately constant DOT during the constant feed. When the biomass concentration reached about 27 g/l the endotoxin concentration was measured according to the LAL test and the endotoxin content was about 900 mg/l.

The growth of the cells was measured by optical density at 500 nm and by dry cell weight measurements. The dry weight measurements was as follows; 5 ml of culture were transferred into a pre-weighed test tube, centrifuged at 4500 rpm for 10 minutes and washed once with distilled water. The test tubes were dried at 105° C. overnight and then weighed.

Glucose concentration was analysed enzymatically in samples from which the cells had been removed by centrifugation, as described by Xu B., at al., Modelling of overflow metabolism in batch and fed-batch cultures of *Escherichia coli.*, Biotechnol. Progress 15, 81–90, 1999.

The limulus ameobocyte lysate (LAL) test, described in "Guideline on validation of the LAL test as an end-product endotoxin test for human and animal parental drugs, biological products, and medical devices" U.S. Department of Health and Human Services, December 1987, was used to determine endotoxin levels. The sensitivity of the LAL test is of the order of magnitude of a few picograms of endotoxin per ml of test sample. The analytical kit produced by Charles River Endosafe Ltd, USA was used to analyse the endotoxin according to the manufacturer recommendations.

EXAMPLE 2

Control Fermentation with Recombinant Protein ZZT2 Producing *E. coli* W3110/pRIT44T2

Bacterial Strain; The *E. coli* K12 strain W3110 [F⁻, IN(rrnD-rrnE)], (Genetic Stock Center, Yale University, New Haven, Conn.). The strain harboured the plasmid pRIT44T2 (Köhler K et al, 1991, Engineering proteins to enhance their partition coefficients in aqueous two-phase systems Bio-technology (NY) 9:642–646) encoding for the recombinant protein ZZT2 and resistance genes for both ampicillin and tetracycline.

Media; Mineral salt medium with following composition in shake flasks for inoculum preparation—2 g/l $Na_2SO_4$, 2.68 g/l $(NH_4)_2SO_4$, 0.5 g/l $NH_4Cl$, 14.6 g/l $K_2HPO_4$, 3.6 g/l $NaH_2PO_4 \cdot H_2O$, 1 g/l $(NH_4)_2$—H-citrate. 2 ml/l of a 1 M solution of $MgSO_4$, 3 ml/l of a trace element solution (se below), 100 mg/l ampicillin, 100 mg/l tryptophan, 100 mg/l thiamine and 10 g/l of glucose. The Fermenter medium had the same compositon as above except for no initial glucose; feeding solution contained 4/l g $Na_2SO_4$, 5.36 g/l $(NH_4)_2SO_4$, 1 g/l $NH_4Cl$, 29.2 g/l $K_2HPO_4$, 7.2 g/l $NaH_2PO_4 \cdot H_2O$, 2 g/l $(NH_4)_2$—H-citrate, 2 ml/l of a 1M solution of $MgSO_4$, 3 ml/l of a trace element solution (Xu B., at al., Modelling of overflow metabolism in batch and fed-batch cultures of *Escherichia coli.*, Biotechnol. Progress 15, 81–90, 1999), 100 mg/l ampicillin, 100 mg/l tryptophan, 100 mg/l thiamine and 500 g/l glucose.

A standard bench-scale fermenter with initial culture volume of 6.6 l. The fermenter was inoculated to initial optical density ($OD_{500}$) of 0.5. pH was kept at 7 by titration 25% ammonia solution. After approximately 1 h batch phase the exponential feeding was started according to the profile $F(t) = F_0 \cdot e^{k \cdot t}$ where $F(t)$ is the time dependent feeding rate, $F_0$ is the initial feeding rate (3 ml/h), k is an exponential rate constant (0.3 l/h) and t is a current time. Exponential feeding phase continued for 10.6 h and was then switched to a constant feed rate of 81.5 ml/h. 2M $MgSO_4$ solution was added intermittently during the cultivation (48 ml in total). The culture was aerated at a flow rate of 3 l/min. Dissolved oxygen tension ($pO_2$) was kept above 30%. The temperature was 35° C. throughout the culturing process. The production of the protein ZZT2 was induced after about 17.5 h ($OD_{500}$ approximately 50) by addition of 3-β-indole acrylic acid to a concentration of 25 mg/l. When the biomass concentration reached 37 g/l after 30 h the endotoxin concentration was measured according to the LAL test and the endotoxin content was about 650 mg/l. At the end of the fermentation the specific protein ZZT2 concentration reached a value of approximately 60 mg/g and the acetic acid concentration was 17 mg/l.

The growth of the cells was measured by optical density at 500 nm and by dry cell weight measurement as follows: 5 ml of culture were transferred into a pre-weighed test tube, centrifugated at 4500 rpm for 10 minutes and washed once with distilled water. The test tubes were dried at 105° C. overnight and then weighed. Glucose and acetic acid concentrations were analysed enzymatically in samples from which the cells had been removed, as described by Xu B., at al., Modelling of overflow metabolism in batch and fed-batch cultures of *Escherichia coli*, Biotechnol. Progress 15, 81–90, 1999. The limulus ameobocyte Sensate (LAL) test, described in "Guideline on validation of the LAL test as an end-product endotoxin test for human and animal parental drugs, biological products, and medical devices" U.S. Department of Health and Human Services, December 1987, was used to determine endotoxin levels. The sensitivity of the LAL test is of the order of magnitude of a few picograms of endotoxin per ml of test sample. The analytical kit produced by Charles River Endosafe Ltd, USA was used to analyse the endotoxin according to the manufacturer recommendations.

EXAMPLE 3

Fermentation of the Recombinant Protein ZZT2 Producing *E. coli* W3110/pRIT44T2 According to the Invention Bacterial Strain; The *E. coli* K12 strain W3110 [F⁻, N(rrnD-rrnE)], (Genetic Stock Center, Yale University, New Haven, Conn.). The strain harboured plasmid pRIT44T2 (Köhler K et al, 1991, Engineering proteins to enhance their partition coefficients in aqueous two-phase systems Bio-technology (NY) 9:642–646) encoding for the recombinant protein ZZT2 and resistance genes for both ampicillin and tetracycline.

Media; Mineral salt medium with the following composition 3.57 g/l $H_3PO_4$, 3.46 g/l $H_2SO4$, 1.60 g/l KOH, 0.50 $MgSO_4 \times 7H_2O$, 3.20 NaOH, 5.20 $(NH_4)_2SO_4$, 10 mg/l thiamine and 100 mg/l ampicillin. The medium also contained the following trace components 90 mg/l $FeSO_4 \times 7H_2O$, 77 mg/l citric acid x $1H_2O$, 7 mg/l $CoCl_2 \times 6H_2O$, 2 mg/l $MnCl_2 \times 4H_2O$, 1 mg/l $ZnCl_2$. The initial glucose concentration was 10.0 g/l. The pH was set to 7.0 after the sterilisation and controlled at 7.0 during the fermentation by titration with 25% $NH_3$ and 2M $H_2SO_4$.

An inoculum culture of 3×250 ml was run in shake flasks until the cell dry weight was about 1.5 g/l. The glucose feed solution for the fed-batch cultivation held a glucose concentration of 500 g/l. The glucose feed also contained 133 mg/l tryptophane to prevent leakage of the promoter before the induction. The *E. coli* strain W3110/pRIT44T2 was cultivated in a 18 liter standard laboratory fermenter obtained from Belach Bioteknik AB, Stockholm. The liquid volume at the beginning of the fed-batch culturing process was 7.0 l, the initial temperature 35° C. and the culturing process was controlled as follows. After about 4 hours the glucose feeding was started to maintain the glucose concentration in the fermenter between 1–5 g/l. When $OD_{620}$ reached a value of about 20 the initial temperature of 35° C. was manually decreased in steps of 1–2° C. to maintain the oxygen consumption rate (OCR) around 100 mmol/lh. The production of the protein ZZT2 was induced at an $OD_{620}$ of about 50 by addition of 25 mg/l 3-β-indole acrylic acid to the fermenter. The temperature was 31° C. at harvest. When the biomass concentration reached 20 g/l after 18 h the endotoxin concentration was measured according to the LAL test and the endotoxin content was about 8 mg/l. At the same time the specific protein ZZT2 concentration was 69 mg/g and the acetic acid concentration was 8.4 g/l.

The growth of the cells was measured by optical density at 620 nm and by dry cell weight measurement as follows; 10 ml of culture were transferred into a pre-weighed test tube, centrifugated at 4500 rpm for 10 minutes and washed once with distilled water. The test tubes were dried at 105° C. for 48 h and then weighed. Glucose concentration was analysed enzymatically in samples from which the cells had been removed with an YSI 2700 glucose analyser. Acetic acid was analysed with HPLC using an RI, AMINEX-H column and 5 mM $H_2SO_4$ 0.6 ml/min. The well know limulus ameobocyte lysate (LAL) test, described in "Guideline on validation of the LAL test as an end-product endotoxin test for human and animal parental drugs, biological products, and medical devices" U.S. Department of Health and Human Services, December 1987, was used to determine endotoxin levels. The sensitivity of the LAL test is of the order of magnitude of a few picograms of endotoxin per ml of test sample. The analytical kit produced by Charles River Endosafe Ltd, USA was used to analyse the endotoxin according to the manufacturer recommendations.

EXAMPLE 4

Control Fermentation of the β-Lactamase Producing *E. coli* W3110/pBR322

Bacterial Strain; The *E. coli* K12 strain W3110 [F⁻, IN(rrnD-rrnE)], (Genetic Stock Center, Yale University, New Haven, Conn.). The strain was transformed with plasmid pBR322 encoding for β-lactamase.

Mineral salt medium with following composition 7 g/l $(NH_4)_2SO_4$, 6.6 g/l $Na_2HPO_4 \times 2H_2O$, 1.6 g/l $KH_2PO_4$, 0.5 g/l $(NH_4)_2$—H-citrate. The medium also contained 2 ml/l of 1M $MgSO_4$ and 2 ml/l of trace components (Xu B., at al., Modelling of overflow metabolism in batch and fed-batch cultures of *Escherichia coli.*, Biotechnol. Progress 15, 81–90, 1999). The pH was adjusted to 7 prior to fermentation and kept constant by the addition of ammonia (25%).

*E. coli* strain W3110/pBR322 was cultivated at 37° C. in the above, mentioned medium C under Material and Methods, using 15 l standard laboratory fermenter obtained from Belach Bioteknik AB, Stockholm. The inoculum was 5 ml of a cell suspension (approx. 0.6 g/l) that had been stored in −80° C. in 20% glycerol solution. The batch phase glucose concentration was 2.5 g/l. The glucose concentration in the feed solution was 300 g/l. The aeration was 0.5 VVM and the stirrer speed was 900 rpm. The temperature was 37° C. throughout the culturing process. The liquid volume in the beginning of the fed-batch process was 8 l. At glucose exhaustion in the initial batch phase, the fed-batch phase was initiated by an exponential feeding profile with a glucose solution of 300 g/L. The exponential factor was 0.6 h⁻¹, the feeding rate at the start was 31.8 ml/h and at 126.6 ml/h the feeding profile was switched to a constant feed. When the biomass reached 23.9 g/l the periplasmatic β-lactamase concentration was 109 U/ml and the acetic acid concentration was 10 mg/l.

The cell growth was measured by optical density at 600 nm and by dry cell weight measurements: 5 ml of culture were transferred into a pre-weighed test tube, centrifugated at 4500 rpm for 10 minutes and washed once with distilled water. The test tubes were dried at 105° C. overnight and then weighed. Glucose concentration was analysed enzymatically in samples from which the cells had been removed, as described by Xu B., at al. Modelling of overflow metabolism in batch and fed-batch cultures of *Escherichia coli.*, Biotechnol. Progress 15, 81–90, 1999. Glucose concentration was analysed enzymatically in samples from which the cells had been removed, as described by Xu B., at al., Modelling of overflow metabolism in batch and fed-batch cultures of *Escherichia coli.*, Biotechnol. Progress 15, 81–90, 1999. The β-lactamase assay was performed as described be G. Georgiou and M L. Schuler, "Release of periplasmic enzymes and other physiological effects of β-lactamase overproduction in *Escherichia coli.*", Biotechnol. Bioeng 32:741+748, 1988.

EXAMPLE 5

Fermentation of the of the β-Lactamase Producing *E. coli* W3110/pBR322 According to the Invention Bacterial Strain; The *E. coli* K12 strain W3110 [F⁻, IN(rrnD-rrnE)], (Genetic Stock Center, Yale University, New Haven, Conn.). The strain harboured plasmid pBR322 encoding for β-lactamase.

Mineral salt medium with following composition 7 g/l $(NH_4)_2SO_4$, 6.6 g/l $Na_2HPO_4 \times 2H_2O$, 1.6 g/l $KH_2PO_4$, 0.5 g/l $(NH_4)_2$—H-citrate. The medium also contained 2 ml/l of 1M $MgSO_4$ and 2 ml/l of trace components (Xu B., at al., Modelling of overflow metabolism in batch and fed-batch cultures of *Escherichia coli.*, Biotechnol. Progress 15, 81–90, 1999). The pH was adjusted to 7 prior to fermentation and kept constant by the addition of ammonia (25%).

*E. coli* strain W3110/pBR322 was cultivated in the above mentioned medium in a 7 liter standard laboratory fermenter obtained from Belach Bioteknik AB, Stockholm. The inoculum was 3 ml of a cell suspension (approx. 0.6 g/l) that had been stored in −80° C. in 20% glycerol solution. The batch phase glucose concentration was 5 g/l. The glucose concentration in the feed solution was 500 g/l. The aeration was 0.75 VVM and the stirrer speed was 600 rpm. The liquid volume at the beginning of the fed-batch culturing process was 4.0 l. During an initial batch phase, the initial glucose was consumed and the initial temperature was set to 37° C. Then the fed-batch was started and the temperature was controlled so that the DOT did not decline below 30% air saturation. The temperature was reduced throughout the remaining cultivation until 25° C. was reached 11 h after the start of the temperature control. The feed of glucose was allowing glucose to accumulate and then maintaining the glucose concentration in the medium in the range of 1–3 g/l. When the biomass concentration reached 25 g/l after 11 h of fed-batch culturing, the endotoxin concentration was about 10 mg/l. At the same time the periplasmatic β-lactamase concentration was approximately 180 U/ml and the acetic acid concentration 0.65 g/l.

The cell growth was measured by optical density at 600 nm and by dry cell weight measurement as follows; 5 ml of culture were transferred into a pre-weighed test tube, centrifugated at 4500 rpm for 10 minutes and washed once with distilled water. The test tubes were dried at 105° C. overnight and then weighed. Glucose and acetat concentrations were analysed enzymatically in samples from which the cells had been removed, as described by Xu B., at al., Modelling of overflow metabolism in batch and fed-batch cultures of *Escherichia coli.*, Biotechnol. Progress 15, 81–90, 1999. The limulus ameobocyte lysate (LAL) test, described in "Guideline on validation of the LAL test as an end-product endotoxin test for human and animal parental drugs, biological products, and medical devices" U.S. Department of Health and Human Services, December 1987, was used to determine endotoxin levels. The sensitivity of the LAL test is of the order of magnitude of a few picograms of endotoxin per ml of test sample. The analytical kit produced by Charles River Endosafe Ltd, USA was used to analyse the endotoxin according to the manufacturer recommendations.

The invention claimed is:
1. A method for growth of bacteria for the production of a product comprising the following steps:
   (a) preparing a culture of bacteria and a growth medium including a carbon/energy source;
   (b) cultivating the culture at a suitable initial temperature;

(c) maintaining the carbon/energy source at a level within the range from about 0.025 to about 2 g/l minimizing the endotoxin release and acetic acid formation and monitoring the oxygen limitation status of the culture of the bacteria;

(d) reducing the initial temperature without limiting the carbon/energy source;

(e) maintaining conditions where oxygen limitation is avoided by increasing and/or reducing the temperature during cultivation; and (f) harvesting the product from the culture.

2. The method according to claim 1, wherein the carbon energy source (c) is maintained at a level within the range from about 0.025 to about 1 g/l.

3. The method according to claim 2, wherein the carbon energy source (c) is maintained at a level within the range from about 0.025 to about 0.25 g/l.

4. The method according to any of claims 1–3, wherein the temperature under (d) is reduced one or more degrees.

5. The method according to claim 4, wherein the temperature is reduced by up to 25° C. from the initial temperature.

6. The method according to claim 1, wherein the oxygen limitation status is monitored by a method selected from dissolved oxygen tension (DOT) and oxygen concentration in the outlet air.

7. The method according to claim 1, wherein the initial temperature (b) is within the range of 20–40° C.

8. The method according to claim 7, wherein the initial temperature (b) is 35° C.

9. The method according to claim 1, wherein the amount of endotoxins in the supernatant is <100 mg/l.

10. The method according to claim 1, wherein the bacteria are Gram negative bacteria.

11. The method according to claim 10, wherein the bacteria are *E. coli* bacteria.

* * * * *